United States Patent [19]

Fujii et al.

[11] 4,411,911
[45] Oct. 25, 1983

[54] METHOD OF TREATING HYPERLIPIDEMIA AND INFLAMMATION WITH SULFONATE DERIVATIVES

[75] Inventors: Setsuro Fujii, Tovonaka; Toshihiro Hamakawa, Naruto; Kazuo Ogawa, Tokushima; Yoshiyuki Muranaka, Tokushima; Sadao Hashimoto, Tokushima, all of Japan

[73] Assignee: Taiho Pharmaceutical Company, Limited, Tokyo, Japan

[21] Appl. No.: 225,979

[22] Filed: Jan. 19, 1981

[30] Foreign Application Priority Data

Jan. 31, 1980 [JP] Japan ................................ 55-11214
Jul. 11, 1980 [JP] Japan ................................ 55-95299
Sep. 30, 1980 [JP] Japan ................................ 55-137026
Dec. 19, 1980 [JP] Japan ................................ 55-180852

[51] Int. Cl.³ .................... A61K 31/35; A61K 31/34; A61K 31/255
[52] U.S. Cl. .................... 424/283; 260/456 R; 260/456 A; 424/285; 424/278; 424/303; 424/300; 549/498; 549/496; 549/488; 549/473; 549/427; 549/426; 549/425; 549/414; 549/511; 549/548; 549/553; 549/554; 549/562
[58] Field of Search ................. 260/345.9 R, 456 R, 260/456 A, 456 P, 340.9 R; 424/283, 285, 278, 300, 303

[56] References Cited

U.S. PATENT DOCUMENTS 3,200,138 8/1965 Wuest ............................. 260/456 R

FOREIGN PATENT DOCUMENTS 617957 4/1961 Canada ............................ 260/456 P

OTHER PUBLICATIONS

Pattison et al., Can. J. Chem., 34, 757 (1956).
Lichtenberger et al., Bull. Soc. Chim. France, pp. 995-1001 (1948).
Crowther et al., J. Chem. Soc., 1963, pp. 2818-2821.
Charlton et al., Can. J. Chem., 58, 458 (1980).
Tuinman et al., Helv. Chim. Acta, 51, 1778 (1968).
Schaffner, Tetrahedron, vol. 30, pp. 1891-1902 (1974).
Prib et al., Chem. Abstract, 78, 57942Y (1973).

*Primary Examiner*—Nicky Chan
*Attorney, Agent, or Firm*—Murray and Whisenhunt

[57] ABSTRACT

Novel sulfonate derivatives represented by the formula $R_1SO_3CH_2CO(CH_2)_nR_2$ act to inhibit esterases and chymotripsin and are useful as antilipemic agents, anti-inflammatory agents, immunity controlling agents, etc.

4 Claims, No Drawings

METHOD OF TREATING HYPERLIPIDEMIA AND INFLAMMATION WITH SULFONATE DERIVATIVES

This invention relates to sulfonate derivatives.

The sulfonate derivatives of the present invention are novel compounds represented by the formula $$R_1SO_3CH_2CO(CH_2)_nR_2 \tag{I}$$

wherein $R_1$ is alkyl having 1 to 4 carbon atoms, alkoxyalkyl having 2 to 6 carbon atoms, aralkyl, cycloalkyl or aryl with or without a substituent (which is alkyl having 1 to 12 carbon atoms, lower alkoxy, halogen, hydroxyl, carboxyl, acetamido, nitro or ethylenedioxymethyl), $R_2$ is alkyl having 1 to 15 carbon atoms, alkenyl having 2 to 15 carbon atoms, halogen, hydroxyl, lower alkoxy, lower alkoxycarbonyl, acyloxy, carbobenzoxyamino, cycloalkyl having 3 to 6 carbon atoms, cyclic alkylether having 2 to 5 carbon atoms, cyclic alkenylether having 2 to 5 carbon atoms or aryl with or without lower alkyl as substituents, and n is 0 or an integer of 1 to 6.

Examples of the groups represented by $R_1$ in the formula (I) include: alkyl groups having 1 to 4 carbon atoms, such as methyl, ethyl, propyl and butyl; alkoxyalkyl groups having 2 to 6 carbon atoms, such as ethoxymethyl, methoxyethyl, ethoxypropyl and methoxybutyl; aralkyl groups having 7 to 10 carbon atoms, benzyl, phenethyl and phenylpropyl, and benzyl and phenethyl which have methyl, ethyl or like substituent on the benzene ring; cycloalkyl groups having 5 to 8 carbon atoms, such as cyclopentyl, cyclohexyl and cyclooctyl; and aryl groups, such as phenyl and naphthyl, examples of substituents therefor being alkyl groups having 1 to 12 carbon atoms, such as methyl, propyl, hexyl, decyl and dodecyl, lower alkoxy groups having 1 to 6 carbon atoms, such as methoxy, ethoxy and hexyloxy, and halogen atoms, such as fluorine, chlorine, bromine and iodine, in addition to those already given.

Examples of the groups represented by $R_2$ in the formula (I) include: alkyl groups having 1 to 15 carbon atoms, such as methyl, ethyl, propyl, hexyl, decyl, dodecyl and pentadecyl; alkenyl groups having 2 to 15 carbon atoms, such as vinyl, allyl, propenyl, butenyl, decenyl and tetradecenyl; halogen atoms, such as fluorine, chlorine, bromine and iodine; lower alkoxy groups having 1 to 5 carbon atoms; lower alkoxycarbonyl groups having 2 to 6 carbon atoms, such as methoxycarbonyl, ethyoxycarbonyl, butoxycarbonyl and pentyloxycarbonyl; acyloxy groups having 2 to 6 carbon atoms, such as acetyloxy, propanoyloxy, butyryloxy and valeryloxy; cycloalkyl groups having 3 to 6 carbon atoms, such as cyclopropyl, cyclobutyl, cyclopentyl and cyclohexyl; cyclic alkylether groups, such as tetrahydrofuranyl and tetrahydropyranyl; cyclic alkenylether groups, such as 2,3-dihydrofuranyl, 2,5-dihydrofuranyl, furanyl, 3,4-dihydro-2H-pyranyl, 3,6-dihydro-2H-pyranyl, 2H-pyranyl, 4H-pyranyl and pyranyl; and aryl groups, such as phenyl and naphthyl, exemplary of substituents therefor being alkyl groups having 1 to 6 carbon atoms. The groups $R_2$ further include those already specified, such as hydroxyl.

The novel compounds of the present invention have esterase inhibiting activity and chymotripsin inhibiting activity and are useful, for example, as antilipemic agents, anti-inflammatory agents and immunity controlling agents.

The compounds of the formula (I) can be prepared by the following processes.

Process A

A process in which a compound represented by the formula $$N_2CHCO(CH_2)_nR_2 \tag{II}$$

wherein $R_2$ and n are as defined above is reacted with a sulfonic acid compound represented by the formula $$R_1SO_3H \cdot mH_2O \tag{III}$$

wherein $R_1$ is as defined above, and m is 0 or an integer of 1 or 2.

Process B

A process in which a compound represented by the formula $$XCH_2CO(CH_2)_nR_2 \tag{IV}$$

wherein X is fluorine, chlorine, bromine or iodine, and $R_2$ and n are as defined above is reacted with a metal salt of a sulfonic acid represented by the formula $$R_1SO_3H \tag{V}$$

wherein $R_1$ is as defined above. Examples of metals of such metal salts are sodium, potassium, magnesium, iron, lead, copper, silver, etc.

The reaction of the process A is conducted usually in a solvent, which is not particularly limited insofar as it does not participate in the reaction. Examples of suitable solvents are dimethyl ether, diethyl ether, tetrahydrofuran, dioxane and like ethers, acetonitrile, chloroform, dichloromethane and like nonprotonic solvents, petroleum ether, ligroine, etc. The compound (II) and the sulfonic acid compound (III) are used preferably in the ratio of at least one mole of the compound (III) per mole of the compound (II). The reaction proceeds advantageously usually at a temperature of about $-10°$ to about 60° C., preferably at about 0° C. to room temperature. Useful compounds (II), some of which are known and some novel, can be prepared from acid chlorides (VI) and diazomethane by the following known reaction.

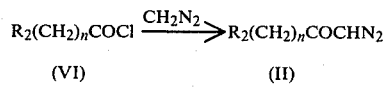

wherein $R_2$ and n are as defined above

The reaction of the acid chloride (VI) with diazomethane is conducted usually in a solvent. Useful solvents are those usable for the reaction between the compound (II) and the compound (III). The acid chloride (VI) and diazomethane are used preferably in the ratio of at least about 2 moles of diazomethane per mole of the acid chloride (VI). The reaction proceeds advantageously at a temperature of about $-10°$ C. to room temperature. The compound (II) produced by the reaction, which can be isolated by a usual separating method such as recrystallization or chromatography, is generally usable as contained in the reaction mixture for the subsequent reaction without isolation.

The reaction of the process B is effected in the absence or presence of a solvent. Suitable solvents, although not particularly limited insofar as they do not participate in the reaction, are methanol, ethanol and like lower alcohols, and acetone, acetonitrile, tetrahydrofuran, dioxane, dimethylformamide and like polar solvents. The compound (IV) and the compound (V) are used preferably in a equimolar ratio. The reaction proceeds advantageously generally at room temperature to the boiling point of the solvent.

Useful compounds (IV) for the process B, some of which are known and some novel, can be prepared, for example, by the following reaction.

M-I

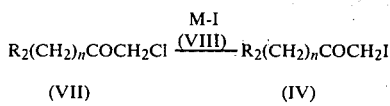

(VII)         (IV)

wherein $R_2$ is as defined above, and M is sodium, potassium or like alkali metal. The reaction between the compound (VII) and the compound (VIII) is effected in the absence or presence of a solvent. Useful solvents, which are not particularly limited provided that they do not participate in the reaction, are methanol, ethanol and like lower alcohols, tetrahydrofuran, dioxane and like polar solvent, acetone, etc. The compound (VII) and the compound (VIII) are used preferably in an equimolar ratio. The reaction is carried out usually at a temperature of about 0° C. to the boiling point of the solvent, preferably at room temperature to about 60° C. The resulting compound (IV) is used as a starting material of the invention, as isolated from, or contained in, the reaction mixture.

The novel compounds (I) prepared by the processes A and B can be isolated by usual methods, such as column chromatography, recrystallization and vacuum distillation.

Among the sulfonate derivatives thus prepared, those in which $R_2$ is acyloxy can be further converted, if desired, to compounds in which $R_2$ is hydroxyl when hydrolyzed in the presence of an acid catalyst. This reaction is carried out usually in a solvent, which is not particularly limited provided that it does not participate in the reaction. Suitable solvents are water-containing alcohols, such as methanol, ethanol, etc. Acids useful for the hydrolysis are those usually serviceable as deacylating agents, such as hydrochloric acid, sulfuric acid, nitric acid, acetic acid and hydrobromic acid. The reaction proceeds advantageously usually at −10° to 50° C., preferably about 0° C. to room temperature.

The compounds of the invention represented by the formula (I) can be prepared also by the following process.

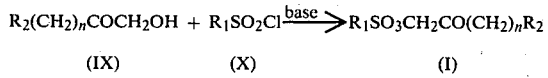

(IX)        (X)         (I)

wherein $R_1$, $R_2$ and n are as defined above, but $R_2$ is not hydroxyl. The reaction between the keto-alcohol (IX) and the sulfonyl chloride (X) is conducted usually in a solvent in the presence of a dehydrochloride agent. The solvent is not particularly limited provided that it does not participate in the reaction. Examples of useful solvents are chloroform, dichloromethane and difluoromethane. Exemplary of useful dehydrochloride agent are pyridine, triethylamine, metal alcoholate, DBU (1,8-diazabicyclo(5,4,0)-7-undecene) and like bases. The keto-alcohol (IX) and the sulfonyl chloride (X) are used preferably in an equimolar ratio. The reaction is carried out at a temperature of −10° to 50° C., preferably at about 0° C. to room temperature.

As already mentioned, the sulfonate compounds of this invention have inhibitory activity on esterases and chymotripsin and are useful as the active components of drugs, such as antilipemic agents, anti-inflammatory agents, immunity controlling agents, etc.

Antilipemic agents containing compounds of the invention will be described below for example, in comparison with those heretofore available.

Hyperlipidemia is known to be a risk factor leading to various adult diseases, such as arteriosclerosis, cardio- and nephro-vascular diseases, diabetes, etc. The drugs for preventing or alleviating hyperlipidemia must have high safety because such drugs are likely to be used for a prolonged period of time in view of the nature of the disease. However, reports have been made on various side effects of nicotinic acid and derivatives thereof, dextran sulfate, and clofibrate and derivatives thereof heretofore widely used as antilipemic agents. Nicotinic acid and its derivatives, for example, produce side effects, such as pruritus and cutaneous flushing due to vasodilatation, gastrointestinal disorders, abnormalities in liver function and glucose intolerance. These drugs have many side effects further because they must be given at a large dose of at least 3 g/day.

Clofibrate, which is typical of widely used antilipemic agents, has recently been reported as having a carcinogenic activity as a serous side effect. Although animal tests or immunological investigations are being carried out by research institutes, the ultimate conclusions still remain to be made, so that clofibrate is clinically in limited use in various countries. In addition to the carcinogenic activity, clofibrate causes an increased sterol discharge, which reportedly increases the likelihood of gallstone formation. Thus the drug is likely to have another side effect.

The antilipemic agents containing compounds of this invention are much more effective than nicotinic acid, derivatives thereof, dextran sulfate, clofibrate and derivatives thereof and have exceedlingly low toxicity and therefore very high safety.

The sulfonate compounds of the invention can be formulated into pharmaceutical preparations suited for various routes of administration. Examples of such preparations are tablets, capsules, granules, powders and liquids for oral administration, and suppositories for non-oral administration.

Examples of useful excipients for preparing tablets, capsules, granules and powders are lactose, sucrose, starch, talc, magnesium stearate, crystalline cellulose, methyl cellulose, carboxymethyl cellulose, glycerin, sodium alginate and gum arabic. Also useful for such preparations are binders, such as polyvinyl alcohol, polyvinyl ether, ethyl cellulose, gum arabic, shellac and sucrose, glazing agents, such as magnesium stearate and talc, and usual coloring agents and disintegrators. Tablets can be coated by a known method. Useful liquid preparations are in the form of aqueous or oily suspensions, solutions, syrup, elixir, etc. These preparations are produced by usual methods.

Examples of useful base materials for preparing suppositories are cacao butter, polyethylene glycol, lanolin, fatty acid triglyceride, witepsol (fat, trade mark of Dynamit Nobel A.G. of Germany), etc.

The dose of the drugs according to the invention can not be specifically defined but varies with the symptoms, body weight, age, etc. of the patient. Usually the active component of such drugs is given in an amount of about 50 to about 1500 mg/day for adults at a time or in two to four divided doses. The dose unit such as tablet or capsule preferably contains about 10 to about 1500 mg of the active component.

Given below are examples in which compounds of this invention are prepared, examples of pharmaceutical preparations, tests for determining antilipemic effect and acute toxicity test.

EXAMPLE 1

A 100 ml quantity of diazomethane ether solution (containing 2.8 g of diazomethane) is prepared from 10 g of N-methyl-N-nitrosourea. To the diazomethane ether solution is added dropwise 1.7 g of n-butyl chloride with ice-cooling, and the mixture is thereafter stirred for 30 minutes. Nitrogen gas is passed through the reaction mixture at room temperature to remove the excess of diazomethane therefrom. The ethereal solution is distilled in a vacuum, and the residue is purified by column chromatography (silica gel, developed with chloroform) to give 1.75 g of light yellow oily 1-diazo-2-pentanone (yield 97.8%).

Mass spectrum (abbr. as MS, M+): 112
NMR (CDCl$_3$) δ(ppm): 5.18 s (2H), 2.22 t (2H), 1.80–1.32 m (2H), 0.88 t (3H).

A 1.1 g portion of the 1-diazo-2-pentanone is dissolved in 30 ml of ether, and 1.6 g of ethanesulfonic acid is slowly added to the solution at room temperature. The mixture is stirred until no nitrogen is evolved. After the reaction, the ethereal layer is washed with water, dried over anhydrous sodium sulfate and distilled in a vacuum to remove the solvent. The oily product is purified by column chromatography (silica gel, developed with chloroform) to give 1.0 g of 2-oxopentylethane sulfonate (Compound 1) in the form of a colorless transparent oil (yield 52.6%).

MS (M+): 194
NMR (CDCl$_3$) δ(ppm): 4.70 s (2H), 3.22 q (2H), 2.42 t (2H), 1.90–1.40 m (2H), 1.44 t (3H), 0.92 t (3H).

EXAMPLE 2

Compounds 2 to 5 are prepared in the same manner as in Example 1.

EXAMPLE 3

A 1.2 g quantity of 1-diazo-2-pentanone is dissolved in 50 ml of ether, and 2.3 g of benzenesulfonic acid monohydrate is slowly added to the solution at room temperature. The same procedure as in Example 1 is thereafter followed to give 2.0 g of 2-oxopentylbenzene sulfonate in the form of a colorless transparent oil (Compound 6). Yield 77.2%.

MS (M+): 242
NMR (CDCl$_3$) δ(ppm): 7.35–8.00 m (5H), 4.49 s (2H), 2.42 t (2H), 1.80–1.32 m (2H), 0.87 t (3H).

EXAMPLE 4

Compounds 7 to 14 are prepared in the same manner as in Example 3.

EXAMPLE 5

A 1.0 g quantity of 1-diazo-2-pentanone is dissolved in 50 ml of chloroform, and 2.2 g of o-toluenesulfonic acid is slowly added to the solution. The same procedure as in Example 1 is thereafter repeated to afford 1.37 g of 2-oxopentyl-o-toluene sulfonate in the form of a transparent colorless oil (Compound 29).

Yield 59.9%.
MS (M+): 256
NMR (CDCl$_3$) δ(ppm): 7.92 d (1H), 7.70–7.20 m (3H), 4.49 s (2H), 2.68 s (3H), 2.46 t (2H), 1.80–1.40 m (2H), 0.90 t (3H).

EXAMPLE 6

Compounds 26 to 28, and 30 to 33 are prepared in the same manner as in Example 5.

EXAMPLE 7

A 1.0 g quantity of 1-diazo-2-hexanone is dissolved in 50 ml of ether, and 2.5 g of p-methoxybenzenesulfonic acid is slowly added to the solution at room temperature. The same procedure as in Example 1 is thereafter repeated to afford 1.6 g of 2-oxahexyl-p-methoxybenzene sulfonate in the form of a colorless transparent oil (Compound 35). Yield 70.3%.

MS (M+): 286
NMR (CDCl$_3$) δ(ppm): 7.80 d (2H), 6.97 d (2H), 4.44 s (2H), 3.82 s (3H), 2.42 t (2H), 1.70–1.00 m (4H), 0.81 t (3H).

EXAMPLE 8

Compounds 34 and 36 to 42 are prepared in the same manner as in Example 7.

EXAMPLE 9

A 1.0 g quantity of 1-diazo-2-octanone is dissolved in 30 ml of dioxane, and 2.0 g of p-ethoxybenzenesulfonic acid is slowly added to the solution at room temperature. The mixture is stirred until no nitrogen is evolved. The reaction mixture is distilled in a vacuum to remove the solvent, and the residue is extracted with 50 ml of ether, washed with water and dried over anhydrous sodium sulfate. The dried product is distilled in a vacuum to remove the solvent and obtain an oily product, which is purified by column chromatography (silica gel, developer solvent chloroform), affording 1.26 g of 2-oxooctyl-p-ethoxybenzene sulfonate (Compound 46), m.p. 38° to 39° C. Yield 59.0%.

MS (M+): 328
NMR (CDCl$_3$) δ(ppm): 7.80 d (2H), 6.95 d (2H), 4.44 s (2H), 4.06 q (2H), 2.44 t (2H), 1.60–1.10 m (8H), 0.82 t (3H).

EXAMPLE 10

Compounds 47 to 58 are prepared in the same manner as in Example 9.

EXAMPLE 11

A 1.2 g quantity of 1-diazo-2-undecanone is dissolved in 50 ml of ether, and 1.6 g of p-chlorobenzenesulfonic acid is slowly added to the solution at room temperature. The mixture is stirred until no nitrogen is evolved. The reaction mixture is washed with water, and the ethereal layer is dried over anhydrous sodium sulfate and distilled in a vacuum to remove the solvent. The residue is recrystallized from ether/petroleum ether to give 1.62 g of 2-oxoundecyl-p-chlorobenzene sulfonate (Compound 68), m.p. 51° to 51.5° C. Yield 75.3%.

MS (M+): 360
NMR (CDCl$_3$) δ(ppm): 7.81 d (2H), 7.46 d (2H), 4.50 s (2H), 2.40 t (2H), 1.70–1.05 m (14H), 0.82 t (3H).

Elementary analysis:

|   | C | H |
|---|---|---|
| Calcd. for $C_{17}H_{25}ClSO_4$ (%) | 56.58 | 6.99 |
| Found (%) | 56.37 | 7.29 |

EXAMPLE 12

Compounds 64 to 67, 69 and 70 are prepared in the same manner as in Example 11.

EXAMPLE 13

A 1.0 g quantity of 1-diazo-2-nonanone is dissolved in 30 ml of ether, and 2.0 g of 2,4,6-trimethylbenzenesulfonic acid dihydrate is slowly added to the solution at room temperature. The same procedure as in Example 1 is thereafter repeated to give 1.4 g of 2-oxononanyl-2,4,6-trimethylbenzene sulfonate in the form of a colorless transparent oil (Compound 77).

Yield 69.0%.
MS (M+): 340
NMR (CDCl$_3$) δ(ppm): 6.93 s (2H), 4.38 s (2H), 2.56 s (6H), 2.46 t (2H), 2.25 s (3H), 2.78–1.00 m (10H), 0.82 t (3H).

EXAMPLE 14

Compounds 78 to 88 are prepared in the same manner as in Example 13.

EXAMPLE 15

A 1.0 g quantity of 1-diazo-2-pentanone is reacted with 2.3 g of 2,3,4,6-tetramethyl-benzenesulfonic acid in 30 ml of ether until nitrogen no longer evolves. The reaction mixture is washed with water, dried and distilled in a vacuum to remove the ether. The residue is recyrstallized from ethanol/water, affording 1.6 g of 2-oxopentyl-2,3,4,6-trimethylbenzene sulfonate (Compound 95), m.p. 49° to 50° C. Yield 60.0%.

MS (M+): 298
NMR (CDCl$_3$) δ(ppm): 6.94 s (1H), 4.38 s (2H), 2.55 s (6H), 2.44 t (2H), 2.24 s (3H), 2.16 s (3H), 1.77–1.35 m (2H), 0.85 t (3H).

EXAMPLE 16

Compounds 93, 94 and 96 to 113 are prepared in the same manner as in Example 15.

EXAMPLE 17

A 1.2 g quantity of 1-chloro-2-pentanone is dissolved in 50 ml of acetone, 1.7 g of potassium iodide is added to the solution, and the mixture is stirred at room temperature for 5 hours. With addition of 2.8 g of silver p-toluenesulfonate, the mixture is stirred at room temperature for 24 hours. The insolubles are filtered off from the reaction mixture, the filtrate is concentrated in a vacuum, and the resulting oily product is purified by column chromatography (silica gel, developer solvent chloroform), affording 2.04 g of 2-oxopentyl-p-toluenesulfonate (Compound 16), m.p. 33° to 35° C. Yield 80.0%.

MS (M+): 256
NMR (CDCl$_3$) δ(ppm): 7.78 d (2H), 7.31 d (2H), 4.43 s (2H), 2.41 s (3H), 2.41 t (2H), 1.80–1.30 m (2H), 0.82 t (3H).

EXAMPLE 18

Compounds 15, and 17 to 25 are prepared in the same manner as in Example 17.

EXAMPLE 19

A 2.2 g quantity of 1-iodo-2-heptanone is reacted with 3.2 g of silver p-ethoxybenzenesulfonate in the same manner as in Example 17. The same procedure as in Example 17 is thereafter repeated to give 2.3 g of 2-oxoheptyl-p-ethoxybenzenesulfonate (Compound 45), m.p. 35° to 35.5° C. Yield 73.2%.

MS (M+): 314
NMR (CDCl$_3$) δ(ppm): 7.80 d (2H), 6.96 d (2H), 4.42 s (2H), 4.06 q (2H), 2.42 t (2H), 1.90–1.04 m (6H), 1.40 t (3H), 0.82 t (3H).

EXAMPLE 20

Compounds 43 and 44 are prepared in the same manner as in Example 19.

EXAMPLE 21

A 1.2 g quantity of 1-chloro-2-pentanone is dissolved in 50 ml of acetone, 1.7 g of potassium iodide is added to the solution, and the mixture is stirred at room temperature for 5 hours. With addition of 2.9 g of silver p-hydroxybenzenesulfonate, the mixture is stirred at room temperature for 12 hours. The insolubles are filtered off from the reaction mixture, the filtrate is concentrated in a vacuum, and the concentrate is extracted with 100 ml of chloroform, washed with water and dried over anhydrous sodium sulfate. The dried product is distilled in a vacuum to remove the solvent. The reslting residue is recrystallized from ethanol/water to afford 1.8 g of 2-oxotridecane-p-hydroxybenzenesulfonate (Compound 59), m.p. 85° to 87° C. Yield 70.0%.

MS (M+): 258
NMR (CDCl$_3$) δ(ppm): 7.65 d (2H), 6.82 d (2H), 4.45 s (2H), 2.40 t (2H), 1.80–1.30 m (2H), 0.82 t (3H), 6.80–7.50 b (1H).

EXAMPLE 22

Compounds 60 to 63 are prepared in the same manner as in Example 21.

EXAMPLE 23

A 6.0 g quantity of 1-chloro-2-pentanone is dissolved in 100 ml of acetone, 8.0 g of potassium iodide is added to the solution, and the mixture is stirred at room temperature for 5 hours. The insolubles are filtered off from the reaction mixture, the filtrate is concentrated in a vacuum, and the concentrate is extracted with 100 ml of ether, washed with sodium thiosulfate and dried over anhydrous sodium sulfate. The dried product is distilled in a vacuum to remove the solvent and obtain an oily product, which is then distilled in a vacuum, giving 6.0 g of 1-iodo-2-pentanone, b.p. 96° to 98° C. at 24 to 25 mm Hg.

Yield 54.3%.
MS (M+): 222
NMR (CDCl$_3$) δ(ppm): 3.80 s (2H), 2.70 t (2H), 1.65 q (2H), 0.92 t (3H).

A 0.4 g quantity of 1-iodo-2-pentanone is dissolved in 30 ml of acetonitrile, 0.7 g of silver 2,4,6-trimethylbenzenesulfonate is added to the solution, and the mixture is stirred at room temperature for 40 hours. The insolubles are filtered off from the reaction mixture, and the filtrate is concentrated in a vacuum to obtain an oily product, which is then extracted with 50 ml of ether, washed with water and dried over anhydrous sodium sulfate. The dried product is distilled in a vacuum to remove the solvent and obtain a residue, which is then recrystallized from ethanol/water, giving 0.5 g of 2-oxopentyl-2,4,6-trimethylbenzenesulfonate (Compound 73), m.p. 57.5° to 58.5° C. Yield 94.0%.

MS (M+): 284

NMR (CDCl$_3$) δ(ppm): 6.89 s (2H), 4.36 s (2H), 2.60 s (6H), 2.48 t (2H), 2.30 s (3H), 1.80–1.32 m (2H), 0.89 t (3H).

Elementary analysis:

|  | C | H |
|---|---|---|
| Calcd. for C$_{14}$H$_{20}$SO$_4$ (%) | 59.13 | 7.09 |
| Found (%) | 58.95 | 7.37 |

EXAMPLE 24

Compounds 71, 72 and 74 to 76 are prepared in the same manner as in Example 23.

EXAMPLE 25

A 2.3 g quantity of 1-chloro-2-dodecanone is dissolved in 100 ml of acetone, 1.7 g of potassium iodide is added to the solution, and the mixture is stirred at room temperature for 5 hours. With addition of 3.3 g of silver 2,3,5,6-tetramethylbenzenesulfonate, the mixture is further stirred at 40° C. for 10 hours. The reaction mixture is treated in the same manner as in Example 17 for purification, giving 2.8 g of 2-oxodecyl-2,3,5,6-tetramethylbenzenesulfonate (Compound 92), m.p. 36° to 37.5° C. Yield 71.5%.

MS (M+): 396,

NMR (CDCl$_3$) δ(ppm): 7.18 s (1H), 4.40 s (2H), 2.50 s (6H), 2.24 s (6H), 2.48 t (2H), 1.80–1.00 m (16H), 0.84 t (3H).

EXAMPLE 26

Compounds 89 to 91 are prepared in the same manner as in Example 25.

Table 1 shows Compounds 1 to 162 which are typical of the sulfonate derivatives of this invention represented by the formula (I). In the table, MS stands for mass spectrum, and the NMR values are δ(ppm) values measured in CDCl$_3$ except that the value for Compound 103 is determined in dimethylformamide-d$_6$.

The above compounds of this invention are tested by the following methods for antilipemic effect and acute toxicity. The results are also listed in Table 1. In the column of antilipemic effect in the table, the asterisked values indicate the effect achieved by orally giving 200 mg/kg of the compounds concerned, and the unmarked values, the effect attained by orally giving 100 mg/kg. In the same column, "TG" stands for percent triglycerides inhibition and "CS" percent cholesterol inhibition.

1. Antilipemic effect

Seven-week-old male Wistar rats weighing 200 to 220 g are used, 5 rats in each group.

Each compound of the invention (100 mg or 200 mg) is dissolved in 10 ml of an olive oil-cholesterol mixture (containing 15% of cholesterol). The mixture containing the compound is orally given to the rat with a probe at a dose of 10 ml/kg. Two or 8 hours thereafter, 6 ml of whole blood is withdrawn from the descending aorta of the rat under ether anesthesia with a syringe containing heparin. The blood is centrifuged at 5° C. and 3000 r.p.m. to obtain the plasma. The plasma collected after the lapse of 2 hours is used for determining the triglycerides content, and the plasma obtained 8 hours later for determining the total cholesterol content, using a triglycerides measuring kit (trade mark "Triglycerdies-B Test Wako," product of Wako Junyaku Co., Ltd., Japan) and a total cholesterol measuring kit (trade mark "Cholesterol Test Wako," product of the same), respectively. The olive oil-cholesterol mixture containing no compound is similarly given to a control group, while no treatment is conducted for a normal group. The triglycerides and total cholesterol contents in the plasma are also determined for these groups in the same manner as is the case with the test groups.

The percent hyperlipidemia inhibition achieved by the present compound is given by $$\text{Percent inhibition} = \frac{A - C}{A - B} \times 100$$

in which A is the triglycerides (cholesterol) content of the control group, B is the triglycerides (cholesterol) content of the normal group, and C is the triglycerides (cholesterol) content of the group to which the present compound is given.

The reslts are given in Table 1, which shows that the tested compounds of the invention achieve an outstanding antilipemic effect.

2. Acute toxicity

Six-week-old male Wistar rats weighing 180 to 200 g are used, 5 rats in each group. Each compound of the invention is suspended in a 30% aqueous solution of polyethylene glycol 6000 and orally given to the rat at the dosage shown in Table 2. The animals are checked for poisoning, body weight and survival to determine the LD$_{50}$ value.

TABLE 1

R$_1$SO$_3$CH$_2$COR$_2$

| A | B | C | D | E | F | G | H a | H b | I |
|---|---|---|---|---|---|---|---|---|---|
| Comp. No. | R$_1$ | R$_2$ | M.P. (°C.) | Yield (%) | NMR —SO$_3$CHCO— | MS (M+) | Antilipemic Effect (%) TG | CS | LD$_{50}$ (mg/kg) |
| 1 | C$_2$H$_5$— | —CH$_2$CH$_2$CH$_3$ | Oil | 52.6 | 4.70 | 194 | 92 | 89 | >1000 |
| 2 | C$_2$H$_5$OCH$_2$CH$_2$CH$_2$— | " | " | 62.2 | 4.71 | 252 | 65* | | |
| 3 | ⟨phenyl⟩— | " | " | 67.7 | 4.67 | 248 | 51* | | |
| 4 | ⟨phenyl⟩—CH$_2$— | " | 44.5–45.5 | 65.7 | 4.50 | 256 | 68 | 52 | |

TABLE 1-continued $R_1SO_3CH_2COR_2$

| Comp. No. | $R_1$ | $R_2$ | M.P. (°C.) | Yield (%) | NMR —$SO_3\underline{CH}CO$— | MS (M+) | Anti-lipemic Effect (%) TG | Anti-lipemic Effect (%) CS | $LD_{50}$ (mg/kg) |
|---|---|---|---|---|---|---|---|---|---|
| 5 | 2-naphthyl | " | 40–41 | 46.0 | 4.49 | 292 | 86 | 73 | >2500 |
| 6 | phenyl | " | Oil | 77.2 | 4.49 | 242 | 90 | 53 | >1000 |
| 7 | " | —$CH_2(CH_2)_2CH_3$ | " | 61.5 | 4.47 | 256 | 98 | 67 | |
| 8 | " | —$CH_2CH_2)_3CH_3$ | " | 62.3 | 4.48 | 270 | 87 | 60 | >2000 |
| 9 | " | —$CH_2(CH_2)_4CH_3$ | " | 70.6 | 4.49 | 284 | 88 | 62 | >3000 |
| 10 | " | —$CH_2(CH_2)_7CH_3$ | 34 | 70.5 | 4.48 | 327 | 80 | 61 | >3000 |
| 11 | " | —$CH_2\underset{CH_3}{\underset{|}{C}}CH_3$ with $CH_3$ | Oil | 60.1 | 4.34 | 270 | 80 | 53 | >3000 |
| 12 | " | —$CH_2CH_2CH(CH_3)_2$ | " | 54.0 | 4.44 | 270 | 95 | 63 | >2500 |
| 13 | " | —CH=CHCH_3 | " | 21.0 | 4.68 | 240 | 72 | | |
| 14 | " | —$CH_2CH_2CH=CH_2$ | " | 65.1 | 4.49 | 254 | 92 | 62 | >2000 |
| 15 | 4-CH_3-phenyl | —$CH_2CH_3$ | " | 74.5 | 4.46 | 242 | 40 | 41 | >1500 |
| 16 | " | —$CH_2CH_2CH_3$ | 33–35 | 80.0 | 4.43 | 256 | 64 | 31 | >1500 |
| 17 | " | —$CH_2(CH_2)_2CH_3$ | Oil | 64.5 | 4.42 | 270 | 61 | 33 | >2000 |
| 18 | " | —$CH_2(CH_2)_3CH_3$ | " | 67.0 | 4.46 | 284 | 94 | 40 | >3000 |
| 19 | " | —$CH_2(CH_2)_4CH_3$ | " | 75.7 | 4.43 | 298 | 78 | 41 | >3000 |
| 20 | " | —$CH_2(CH_2)_5CH_3$ | 36–37 | 68.0 | 4.47 | 312 | 71 | 47 | >3000 |
| 21 | " | —$CH_2(CH_2)_6CH_3$ | 32–33 | 70.0 | 4.45 | 326 | 70* | 43* | >3000 |
| 22 | " | —$CH_2(CH_2)_7CH_3$ | 50–51 | 71.0 | 4.45 | 340 | 62* | | >3000 |
| 23 | " | —$CH_2(CH_2)_8CH_3$ | 47–48 | 67.0 | 4.45 | 354 | 64* | | >3000 |
| 24 | " | —$CH_2(CH_2)_{10}CH_3$ | 51–52 | 69.0 | 4.43 | 382 | 63* | | >3000 |
| 25 | " | —$CH_2(CH_2)_{12}CH_3$ | 58–59 | 70.0 | 4.43 | 410 | 62* | | >3000 |
| 26 | " | —$CH(CH_2)_3CH_3$ with $C_2H_5$ | Oil | 68.3 | 4.54 | 312 | 85 | 72 | >4000 |
| 27 | " | —$CH_2(CH_2)_5CH(CH_3)_2$ | " | 60.0 | 4.46 | 340 | 59* | | >3000 |
| 28 | " | —$CH_2(CH_2)_7CH=CH_2$ | 40–40.5 | 62.0 | 4.44 | 352 | 61* | | >3000 |
| 29 | 2-CH_3-phenyl | —$CH_2CH_2CH_3$ | Oil | 59.9 | 4.49 | 256 | 73 | 30 | >1500 |
| 30 | " | —$CH_2(CH_2)_2CH_3$ | " | 52.0 | 4.50 | 270 | 70 | 36 | >1500 |
| 31 | " | —$CH_2(CH_2)_4CH_3$ | " | 66.0 | 4.50 | 298 | 61 | 31 | >2000 |
| 32 | " | —$CH(CH_2)_3CH_3$ with $C_2H_5$ | " | 58.0 | 4.58 | 312 | 70 | 43 | >3000 |
| 33 | " | —$CH_2(CH_2)_5CH(CH_3)_2$ | " | 60.0 | 4.49 | 340 | 67* | | >3000 |
| 34 | 4-CH_3O-phenyl | —$CH_2CH_2CH_3$ | " | 61.8 | 4.42 | 272 | 72 | 68 | >1500 |
| 35 | " | —$CH_2(CH_2)_2CH_3$ | " | 70.3 | 4.44 | 286 | 87 | 72 | >2000 |
| 36 | " | —$CH_2(CH_2)_3CH_3$ | " | 71.3 | 4.43 | 300 | 78 | 79 | >2000 |
| 37 | " | —$CH_2(CH_2)_5CH_3$ | " | 69.0 | 4.43 | 328 | 62 | 62 | >3000 |
| 38 | " | —$CH_2(CH_2)_7CH_3$ | 46–47 | 73.3 | 4.43 | 356 | 67* | | >4000 |
| 39 | " | —$CH_2(CH_2)_9CH_3$ | 52–53 | 60.0 | 4.44 | 384 | 58* | | >4000 |
| 40 | " | —$CH_2CH_2CH(CH_3)_2$ | Oil | 71.5 | 4.46 | 300 | 72 | 70 | >2000 |
| 41 | " | —$CH_2CH_2CH=CH_2$ | " | 63.0 | 4.44 | 284 | 82 | 61 | >2000 |
| 42 | " | —$CH_2(CH_2)_7CH=CH_2$ | 30–31.5 | 60.5 | 4.44 | 368 | 57* | | >4000 |

TABLE 1-continued $R_1SO_3CH_2COR_2$

| Comp. No. | $R_1$ | $R_2$ | M.P. (°C.) | Yield (%) | NMR $-SO_3C\underline{H}CO-$ | MS ($M^+$) | Anti-lipemic Effect (%) TG | Anti-lipemic Effect (%) CS | $LD_{50}$ (mg/kg) |
|---|---|---|---|---|---|---|---|---|---|
| 43 | $C_2H_5O-\text{C}_6\text{H}_4-$ | $-CH_2CH_2CH_3$ | 37–37.5 | 68.0 | 4.42 | 286 | 97 | 120 | >2000 |
| 44 | " | $-CH_2(CH_2)_2CH_3$ | 36–36.5 | 76.0 | 4.44 | 300 | 99 | 90 | >2000 |
| 45 | " | $-CH_2(CH_2)_3CH_3$ | 35–35.5 | 73.2 | 4.42 | 314 | 85 | 80 | >3000 |
| 46 | " | $-CH_2(CH_2)_4CH_3$ | 38–39 | 59.0 | 4.44 | 328 | 65 | 62 | >3000 |
| 47 | " | $-CH_2(CH_2)_5CH_3$ | 41 | 51.0 | 4.44 | 342 | 82* | 60 | >4000 |
| 48 | " | $-CH_2(CH_2)_8CH_3$ | 65–66.5 | 59.0 | 4.43 | 384 | 72* | 55 | >4000 |
| 49 | " | $-CHCH_2CH_3$ $\mid$ $CH$ | Oil | 68.5 | 4.55 | 300 | 90 | 96 | >2000 |
| 50 | " | $-CH(CH_2)_3CH_3$ $\mid$ $C_2H_5$ | " | 66.0 | 4.52 | 342 | 80 | 94 | >4500 |
| 51 | " | $-CH_2(CH_2)_5CH(CH_3)_2$ | " | 85.0 | 4.44 | 370 | 70* | 62 | >4000 |
| 52 | " | $-CH_2CH_2CH=CH_2$ | " | 65.0 | 4.43 | 298 | 95 | 97 | >2000 |
| 53 | $n-C_4H_9O-\text{C}_6\text{H}_4-$ | $-CH_2CH_2CH_3$ | 28–29 | 64.3 | 4.43 | 314 | 61 | 42 | >2000 |
| 54 | " | $-CH_2(CH_2)_2CH_3$ | Oil | 68.3 | 4.43 | 328 | 48 | | >2000 |
| 55 | " | $-CH_2(CH_2)_3CH_3$ | 45–46 | 67.5 | 4.42 | 342 | 69* | 40* | >3000 |
| 56 | " | $-CH_2(CH_2)_5CH_3$ | 55–56 | 69.3 | 4.43 | 370 | 64* | 42* | >3000 |
| 57 | " | $-CH_2(CH_2)_7CH_3$ | 62–63 | 75.0 | 4.44 | 398 | 52* | | >4000 |
| 58 | " | $-CH_2CH_2CH(CH_3)_2$ | Oil | 75.0 | 4.44 | 342 | 61* | | >4000 |
| 59 | $HO-\text{C}_6\text{H}_4-$ | $-CH_2CH_2CH_3$ | 85–87 | 70.0 | 4.45 | 258 | 70 | | >3000 |
| 60 | " | $-CH_2(CH_2)_3CH_3$ | 81–83 | 81.0 | 4.50 | 286 | 83 | | >3000 |
| 61 | " | $-CH_2(CH_2)_6CH_3$ | 52–53 | 78.0 | 4.51 | 328 | 67 | | >3000 |
| 62 | " | $-CH_2(CH_2)_9CH_3$ | 51–52 | 75.0 | 4.50 | 370 | 72* | | >3000 |
| 63 | " | $-CHCH_2CH_3$ $\mid$ $CH_3$ | 84–86 | 68.0 | 4.62 | 272 | 76 | | >2000 |
| 64 | $Cl-\text{C}_6\text{H}_4-$ | $-CH_2CH_2CH_3$ | Oil | 81.1 | 4.50 | 276 | 82 | 56 | >1000 |
| 65 | " | $-CH_2(CH_2)_2CH_3$ | 37–38 | 58.0 | 4.50 | 290 | 87 | 49 | >1000 |
| 66 | " | $-CH_2(CH_2)_3CH_3$ | 31–32 | 69.2 | 4.50 | 304 | 88 | | >1000 |
| 67 | " | $-CH_2(CH_2)_4CH_3$ | 47–48 | 66.9 | 4.52 | 318 | 80 | | >2000 |
| 68 | " | $-CH_2(CH_2)_7CH_3$ | 51–51.5 | 73.5 | 4.50 | 360 | 62 | | >3000 |
| 69 | " | $-CH_2(CH_2)_8CH_3$ | 53–53.5 | 71.0 | 4.48 | 374 | 77* | | >3000 |
| 70 | " | $-CH_2CH_2CH(CH_3)_2$ | 29–30 | 50.0 | 4.48 | 304 | 82 | 47 | >2000 |
| 71 | 2,4,6-(CH$_3$)$_3$-C$_6$H$_2$- | $-CH_3$ | 48–49 | 56.8 | 4.40 | 256 | 60 | 82 | |
| 72 | " | $-CH_2CH_3$ | 47–48 | 70.0 | 4.38 | 270 | 91 | 90 | >3000 |
| 73 | " | $-CH_2CH_2CH_3$ | 57.5–58.5 | 94.0 | 4.36 | 284 | 92 | 90 | >3000 |
| 74 | " | $-CH_2(CH_2)_2CH_3$ | 33–34 | 76.4 | 4.38 | 298 | 77 | 87 | >3000 |
| 75 | " | $-CH_2(CH_2)_3CH_3$ | Oil | 72.8 | 4.35 | 312 | 53 | 60 | >3000 |
| 76 | " | $-CH_2(CH_2)_4CH_3$ | " | 70.0 | 4.36 | 326 | 55 | 62 | >4000 |
| 77 | " | $-CH_2(CH_2)_5CH_3$ | " | 69.0 | 4.38 | 340 | 80 | 74 | >4000 |
| 78 | " | $-CH_2(CH_2)_6CH_3$ | 30–31 | 54.0 | 4.38 | 354 | 56 | 61 | >4000 |

TABLE 1-continued $R_1SO_3CH_2COR_2$

| Comp. No. | $R_1$ | $R_2$ | M.P. (°C.) | Yield (%) | NMR $-SO_3C\underline{H}CO-$ | MS ($M^+$) | Anti-lipemic Effect (%) a TG | Anti-lipemic Effect (%) b CS | $LD_{50}$ (mg/kg) |
|---|---|---|---|---|---|---|---|---|---|
| 79 | " | $-CH_2(CH_2)_7CH_3$ | 34–35 | 61.3 | 4.38 | 368 | 61* | | >4000 |
| 80 | " | $-CH_2(CH_2)_8CH_3$ | 35–36 | 87.0 | 4.39 | 382 | 63* | | >4000 |
| 81 | " | $-CH_2(CH_2)_9CH_3$ | 48–49 | 68.0 | 4.39 | 396 | 60* | | >4000 |
| 82 | " | $-CH_2C(CH_3)_2CH_3$ (neopentyl) | 46–47 | 51.0 | 4.38 | 312 | 56 | 66 | >3000 |
| 83 | " | $-CH_2CH_2CH(CH_3)_2$ | 39–40 | 58.5 | 4.34 | 312 | 68 | 71 | >3000 |
| 84 | " | $-CH(C_2H_5)(CH_2)_3CH_3$ | 33–34 | 74.1 | 4.48 | 340 | 59 | | >4000 |
| 85 | " | $-CH_2(CH_2)_5CH(CH_3)_2$ | Oil | 84.0 | 4.39 | 368 | 48 | | >4000 |
| 86 | " | $-CH_2CH_2CH=CH_2$ | 38–39 | 61.0 | 4.40 | 296 | 79 | 66 | >3000 |
| 87 | " | $-CH_2CH=CH(CH_2)_3CH_3$ | Oil | 20.8 | 4.44 | 338 | 57* | | |
| 88 | " | $-CH_2(CH_2)_7CH=CH_2$ | 38–39 | 63.0 | 4.39 | 380 | 66* | | >4000 |
| 89 | 2,3,4,5,6-pentamethylphenyl (CH₃×4 shown) | $-CH_2CH_2CH_3$ | 59–60 | 70.0 | 4.39 | 298 | 56* | | >3000 |
| 90 | " | $-CH_2(CH_2)_3CH_3$ | Oil | 75.0 | 4.40 | 326 | 59* | | >3000 |
| 91 | " | $-CH_2(CH_2)_5CH_3$ | " | 67.0 | 4.39 | 354 | 47* | | >3000 |
| 92 | " | $-CH_2(CH_2)_8CH_3$ | 36–37.5 | 71.5 | 4.40 | 396 | 43* | | >3000 |
| 93 | " | $-CH_2CH_2CH=CH_2$ | 40–41 | 63.5 | 4.39 | 310 | 60* | | >3000 |
| 94 | " | $-CH_2(CH_2)_5CH(CH_3)_2$ | Oil | 51.0 | 4.38 | 382 | 51* | | >3000 |
| 95 | pentamethylphenyl | $-CH_2CH_2CH_3$ | 49–50 | 60.0 | 4.38 | 298 | 96 | 97 | >3000 |
| 96 | " | $-CH_2(CH_2)_2CH_3$ | 32–33 | 56.0 | 4.38 | 312 | 68 | 71 | >3000 |
| 97 | " | $-CH_2(CH_2)_4CH_3$ | 42–43 | 61.0 | 4.38 | 340 | 55 | 47 | >3000 |
| 98 | " | $-CH_2(CH_2)_6CH_3$ | 36–37 | 70.4 | 4.38 | 368 | 70* | 71* | >4000 |
| 99 | " | $-CH(CH_3)CH_2CH_3$ | 39–40 | 66.3 | 4.49 | 312 | 72 | 78 | >3000 |
| 100 | " | $-CH(C_2H_5)(CH_2)_3CH_3$ | 35–37 | 70.5 | 4.47 | 354 | 66* | 42* | >4000 |
| 101 | " | $-CH_2(CH_2)_7CH=CH_2$ | 28–29 | 59.5 | 4.38 | 394 | 54* | | >4000 |
| 102 | 3-HOOC-C₆H₄- | $-CH_2CH_2CH_3$ | 107–108 | 58.8 | 4.48 | 286 | 42* | | >3000 |
| 103 | 4-CH₃CONH-C₆H₄- | $-CH_2CH_2CH_3$ | 118–119 | 52.4 | 4.71 | 299 | 51* | | >3000 |
| 104 | 4-n-C₁₂H₂₅-C₆H₄- | " | Oil | 61.1 | 4.42 | 410 | 56* | | >3000 |

TABLE 1-continued
R₁SO₃CH₂COR₂
| Comp. No. | R₁ | R₂ | M.P. (°C.) | Yield (%) | NMR —SO₃CHCO— | MS (M⁺) | Anti-lipemic Effect (%) TG | Anti-lipemic Effect (%) CS | LD₅₀ (mg/kg) |
|---|---|---|---|---|---|---|---|---|---|
| 105 | 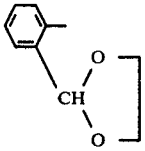 | " | " | 42.9 | 4.43 | 314 | 55* | | >3000 |
| 106 | 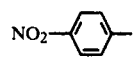 | " | 93–94 | 58.0 | 4.66 | 287 | 60* | | |
| 107 | 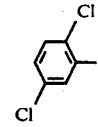 | " | 95–96 | 45.1 | 4.60 | 311 | 75 | | >1500 |
| 108 | 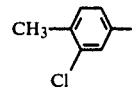 | " | Oil | 64.3 | 4.45 | 290 | 64 | | >1500 |
| 109 | 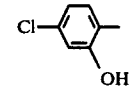 | " | 62–64 | 57.5 | 4.61 | 292 | 82* | | >2000 |
| 110 | 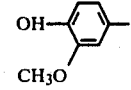 | " | Oil | 58.4 | 4.42 | 288 | 70 | | |
| 111 | 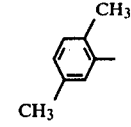 | " | 63–64 | 62.0 | 4.40 | 270 | 73 | 51 | >2000 |
| 112 | 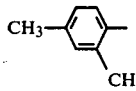 | " | 44–45 | 61.0 | 4.40 | 270 | 80 | 62 | >2000 |
| 113 | 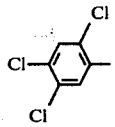 | " | 80–81 | 65.0 | 4.72 | 345 | 60 | | >1500 |
| 114 | 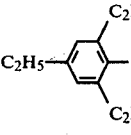 | " | Oil | 40.3 | 4.45 | 326 | 87 | 76 | >3000 |
| 115 | 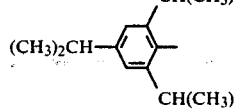 | " | 29–30 | 49.0 | 4.43 | 368 | 67* | | >3000 |

TABLE 1-continued $R_1SO_3CH_2COR_2$

| A | B | C | D | E | F | G | H a b | | I |
|---|---|---|---|---|---|---|---|---|---|
| | | | | | | | Anti-lipemic Effect (%) | | |
| Comp. No. | $R_1$ | $R_2$ | M.P. (°C.) | Yield (%) | NMR $-SO_3\underline{CH}CO-$ | MS ($M^+$) | TG | CS | $LD_{50}$ (mg/kg) |
| 116 | 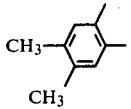 | | 61 | 44.0 | 4.42 | 284 | 90 | 82 | >2000 |
| 117 | 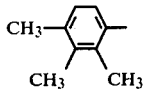 | " | 55–56 | 50.0 | 4.42 | 284 | 70 | 71 | >2000 |
| 118 | 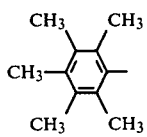 | " | 87–88 | 50.0 | 4.38 | 312 | 76* | | >3000 |
| 119 | 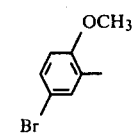 | " | 65.5–66.5 | 39.0 | 4.64 | 350 | 67 | | >2000 |
| 120 | 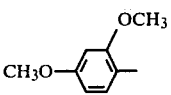 | $-CH_2(CH_2)_6CH_3$ | 44.5–45.5 | 55.3 | 4.50 | 386 | 66* | | >2000 |
| 121 | 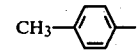 | $-CHCH_2CH_3$<br>\|<br>$C_2H_5$ | Oil | 62.4 | 4.58 | 284 | 63 | 66 | >3000 |
| 122 | " | $-CH(CH_2)_2CH_3$<br>\|<br>$CH_3$ | Oil | 62.4 | 4.61 | 284 | 65 | 51 | >3000 |
| 123 | " | $-CH(CH_2)_2CH_3$<br>\|<br>$C_2H_5$ | " | 68.9 | 4.55 | 298 | 67 | 60 | >3000 |
| 124 | " | $-CH(CH_2)_2CH_3$<br>\|<br>$n-C_3H_7$ | " | 55.0 | 4.57 | 312 | 62 | 42 | >3000 |
| 125 | " | $-CH_2CHCH_2CH_3$<br>\|<br>$CH_3$ | " | 59.0 | 4.47 | 284 | 68 | 44 | >3000 |
| 126 | " | $-CH_2CH_2CHCH_3$<br>\|<br>$CH_3$ | " | 63.5 | 4.50 | 284 | 61 | 47 | >3000 |
| 127 | " | $-CH(CH_2)_3CH_3$<br>\|<br>$CH_3$ | " | 68.0 | 4.56 | 298 | 92 | 67 | >3000 |
| 128 | " | $-CH(CH_2)_3CH_3$<br>\|<br>$n-C_3H_7$ | " | 53.0 | 4.55 | 326 | 62 | 51 | >3000 |
| 129 | " | $-CH(CH_2)_3CH_3$<br>\|<br>$n-C_4H_9$ | " | 45.5 | 4.54 | 340 | 66 | 45 | >3000 |
| 130 | " | $-CH(CH_2)_4CH_3$<br>\|<br>$CH_3$ | " | 75.4 | 4.60 | 312 | 72 | 51 | >3000 |

TABLE 1-continued $R_1SO_3CH_2COR_2$

| A | B | C | D | E | F | G | H a Anti-lipemic Effect (%) | | I |
|---|---|---|---|---|---|---|---|---|---|
| Comp. No. | $R_1$ | $R_2$ | M.P. (°C.) | Yield (%) | NMR $-SO_3C\underline{H}CO-$ | MS (M+) | TG | CS | $LD_{50}$ (mg/kg) |
| 131 | $C_2H_5O-\langle\bigcirc\rangle-$ | $-\underset{\underset{C_2H_5}{\mid}}{C}HCH_2CH_3$ | 60 | 59.5 | 4.53 | 314 | 110 | 97 | >2000 |
| 132 | " | $-\underset{\underset{CH_3}{\mid}}{C}H_2CHCH_3$ | Oil | 61.6 | 4.31 | 300 | 87 | 90 | >2000 |
| 133 | " | $-\underset{\underset{CH_3}{\mid}}{C}H(CH_2)_2CH_3$ | " | 56.5 | 4.60 | 314 | 111 | 91 | >4500 |
| 134 | " | $-\underset{\underset{C_2H_5}{\mid}}{C}H(CH_2)_2CH_3$ | 45–47 | 72.0 | 4.57 | 328 | 82 | 65 | >4500 |
| 135 | " | $-\underset{\underset{n-C_3H_7}{\mid}}{C}H(CH_2)_2CH_3$ | 27–28 | 55.5 | 4.54 | 342 | 91 | 92 | >4500 |
| 136 | " | $-\underset{\underset{CH_3}{\mid}}{C}H_2CHCH_2CH_3$ | Oil | 68.4 | 4.43 | 314 | 80 | 99 | >4500 |
| 137 | " | $-\underset{\underset{C_2H_5}{\mid}}{C}H_2CHCH_2CH_3$ | " | 63.2 | 4.47 | 328 | 81 | 72 | >4000 |
| 138 | " | $-\underset{\underset{CH_3}{\mid}}{C}H_2CH_2CHCH_3$ | " | 65.5 | 4.39 | 314 | 95 | 90 | >2000 |
| 139 | " | $-\underset{\underset{CH_3}{\mid}}{C}H(CH_2)_3CH_3$ | " | 80.0 | 4.56 | 328 | 84 | 87 | >3000 |
| 140 | " | $-\underset{\underset{n-C_3H_7}{\mid}}{C}H(CH_2)_3CH_3$ | " | 69.0 | 4.56 | 356 | 67 | 61 | >3000 |
| 141 | " | $-\underset{\underset{n-C_4H_9}{\mid}}{C}H(CH_2)_3CH_3$ | " | 51.0 | 4.53 | 370 | 68 | 66 | >3000 |
| 142 | " | $-\underset{\underset{CH_3}{\mid}}{C}H_2CH(CH_2)_2CH_3$ | " | 56.3 | 4.43 | 328 | 47 | | >4000 |
| 143 | " | $-\underset{\underset{CH_3}{\mid}}{C}H_2CH_2CHCH_2CH_3$ | " | 62.0 | 4.44 | 328 | 62* | | >4000 |
| 144 | " | $-\underset{\underset{C_2H_5}{\mid}}{C}H_2CH_2CHCH_2CH_3$ | " | 58.5 | 4.45 | 342 | 55* | | >4000 |
| 145 | " | $-\underset{\underset{CH_3}{\mid}}{C}H_2(CH_2)_2CHCH_3$ | " | 62.6 | 4.44 | 328 | 61 | 62 | >3000 |
| 146 | " | $-\underset{\underset{CH_3}{\mid}}{C}H(CH_2)_4CH_3$ | " | 68.6 | 4.56 | 342 | 85 | 77 | >4000 |
| 147 | $\underset{CH_3}{\underset{\mid}{CH_3-\langle\bigcirc\rangle-}}\overset{CH_3}{\overset{\mid}{\phantom{-}}}$ | $-\underset{\underset{CH_3}{\mid}}{C}HCH_2CH_3$ | 30–31 | 67.7 | 4.51 | 298 | 98 | 72 | >3000 |

TABLE 1-continued $R_1SO_3CH_2COR_2$

| A | B | C | D | E | F | G | H a Anti-lipemic Effect (%) TG | H b Anti-lipemic Effect (%) CS | I |
|---|---|---|---|---|---|---|---|---|---|
| Comp. No. | $R_1$ | $R_2$ | M.P. (°C.) | Yield (%) | NMR $-SO_3C\underline{H}CO-$ | MS (M+) | TG | CS | $LD_{50}$ (mg/kg) |
| 148 | " | $-\underset{\underset{C_2H_5}{\vert}}{CH}CH_2CH_3$ | 51 | 65.8 | 4.50 | 312 | 96 | 80 | >3000 |
| 149 | " | $-CH_2\underset{\underset{CH_3}{\vert}}{CH}CH_3$ | 35.5–37 | 62.0 | 4.38 | 298 | 81 | 67 | >3000 |
| 150 | " | $-\underset{\underset{CH_3}{\vert}}{CH}(CH_2)_2CH_3$ | 48–49 | 70.0 | 4.52 | 312 | 84 | 79 | >3000 |
| 151 | " | $-\underset{\underset{C_2H_5}{\vert}}{CH}(CH_2)_2CH_3$ | 47–48 | 72.4 | 4.50 | 326 | 83 | 77 | >3000 |
| 152 | " | $-\underset{\underset{n-C_3H_7}{\vert}}{CH}(CH_2)_2CH_3$ | 48–49 | 61.0 | 4.50 | 340 | 78 | 69 | >4000 |
| 153 | " | $-CH_2\underset{\underset{CH_3}{\vert}}{CH}CH_2CH_3$ | Oil | 63.0 | 4.33 | 312 | 82 | 83 | >4000 |
| 154 | " | $-CH_2\underset{\underset{C_2H_5}{\vert}}{CH}CH_2CH_3$ | " | 65.0 | 4.40 | 326 | 76 | 70 | >4000 |
| 155 | " | $-\underset{\underset{CH_3}{\vert}}{CH}(CH_2)_3CH_3$ | 29–30 | 58.5 | 4.50 | 326 | 67 | 71 | >3000 |
| 156 | " | $-\underset{\underset{n-C_3H_7}{\vert}}{CH}(CH_2)_3CH_3$ | 30–31 | 62.3 | 4.50 | 354 | 58 | 62 | 4000 |
| 157 | " | $-\underset{\underset{n-C_4H_9}{\vert}}{CH}(CH_2)_3CH_3$ | 44.5–45.5 | 54.0 | 4.50 | 368 | 67 | 66 | >4000 |
| 158 | " | $-CH_2\underset{\underset{CH_3}{\vert}}{CH}(CH_2)_2CH_3$ | Oil | 56.7 | 4.39 | 326 | 74 | 70 | >4000 |
| 159 | " | $-CH_2CH_2\underset{\underset{CH_3}{\vert}}{CH}CH_2CH_3$ | " | 69.0 | 4.42 | 326 | 49 | 51 | >4000 |
| 160 | " | $-CH_2CH_2\underset{\underset{C_2H_5}{\vert}}{CH}CH_2CH_3$ | " | 71.0 | 4.41 | 340 | 42 | 40 | >4000 |
| 161 | " | $-CH_2(CH_2)_2\underset{\underset{CH_3}{\vert}}{CH}CH_3$ | " | 59.8 | 4.39 | 326 | 51 | 56 | >3000 |
| 162 | " | $-\underset{\underset{CH_3}{\vert}}{CH}(CH_2)_4CH_3$ | 31.5–33 | 79.1 | 4.52 | 340 | 75 | 77 | >4000 |

Given below are typical examples of pharmaceutical preparations of the invention.

Preparation 1

An encapsulated preparation is formulated by enclosing the following composition (500 mg) in each of soft capsules by a usual method.
   Compound 136: 250 mg,
   Olive oil: 250 mg.

Preparation 2

Tablets are prepared by a usual method, each from the following composition weighing 406 mg.
   Compound 149: 100 mg,
   Soft silicic anhydride: 80 mg,
   Crystalline cellulose: 140 mg,
   Lactose: 80 mg,
   Talc: 2 mg, Magnesium stearate: 4 mg.

Preparation 3

A granular preparation is formulated by a usual method, as enclosed in wrappers each containing the following composition (1000 mg).

Compound 135: 200 mg,
Soft silicic anhydride: 170 mg,
Crystalline cellulose: 350 mg,
Lactose: 270 mg.
Magnesium stearate: 10 mg.

Preparation 4

Suppositories are prepared by a usual method, each from the following composition weighing 2000 mg.

Compound 73: 1000 mg,
Witepsol W-35: 1000 mg.

Preparation 5

An elixir preparation is formulated by a usual method, as enclosed in vials each containing the following composition (20 ml).

Compound 50: 300 mg,
Ethanol: 0.5 ml,
Granular sugar: 2000 mg,
Nikkol HCO-60 (Nikko Chemicals Co., Ltd.): 150 mg,
Flavour: 0.01 ml,
Purified water: q.s.

Given below are reference examples and examples in which other compounds of the invention are prepared.

REFERENCE EXAMPLE 1

A 100 ml quantity of diazomethane ether solution (containing 2.8 g of diazomethane) is prepared from 10 g of N-methyl-N-nitrosourea. To the diazomethane ether solution is added dropwise 1.6 g of cyclopropylcarbonyl chloride with ice-cooling, and the mixture is thereafter stirred for 30 minutes. Nitrogen gas is passed through the reaction mixture at room temperature to remove the excess of diazomethane therefrom. The ethereal solution is distilled in a vacuum, quantitatively affording cyclopropyl diazomethyl ketone in the form of a light yellow oil (Compound A).

MS (M+): 110,

H-NMR (CDCl$_3$) δ(ppm): 5.35 s (1H), 2.35–1.95 m (1H), 1.25–0.08 m (4H).

Compounds B to H listed in Table 2 are also prepared in the same manner as above.

REFERENCE EXAMPLE 2

A 100 ml quantity of diazomethane ether solution (containing 2.8 g of diazomethane) is prepared from 10 g of N-methyl-N-nitrosourea. To the diazomethane ether solution is added dropwise 1.5 g of γ-chloro-n-butyroyl chloride with ice-cooling, and the mixture is thereafter stirred for 30 minutes. Nitrogen gas is passed through the reaction mixture at room temperature to remove the excess of diazomethane therefrom. The ethereal solution is distilled in a vacuum, quantitatively affording γ-chloro-n-propyl diazomethyl ketone in the form of a light yellow oil (Compound I).

MS (M+): 146

H-NMR (CDCl$_3$) δ(ppm): 5.25 s (1H), 3.56 t (2H), 2.50 t (2H), 2.28–1.95 m (2H).

Compounds J to N listed in Table 2 are also prepared in the same manner as above.

EXAMPLE 27

A 1.8 g quantity of 1-diazo-4-cyclohexyl-2-butanone is dissolved in 50 ml of ether, 2.1 g of benzenesulfonic acid monohydrate is slowly added to the solution at room temperature, and the mixture is stirred until nitrogen is no longer evolved. After the reaction, the ethereal layer is washed with water, dried over anhydrous sodium sulfate and distilled in a vacuum to obtain an oily product, which is then recrystallized from ethanol/water, affording 2.0 g of 2-oxo-4-cyclohexylbutylbenzenesulfonate (Compound 164), m.p. 46° to 47° C. Yield 64.5%.

MS (M+): 310,

H-NMR (CDCl$_3$) δ(ppm): 8.10–7.40 m (5H), 4.50 s (2H), 2.44 t (2H), 1.95–0.70 m (13H).

Elementary analysis:

|  | C | H |
| --- | --- | --- |
| Calcd. for C$_{16}$H$_{22}$SO$_4$ (%) | 61.90 | 7.14 |
| Found (%) | 61.74 | 7.29 |

EXAMPLE 28

Compounds 163 and 165 to 171 are prepared in the same manner as in Example 27.

EXAMPLE 29

A 1.52 g quantity of 1-diazo-3-cyclopentylacetone is dissolved in 50 ml of ether, 2.4 g of p-ethoxybenzenesulfonic acid is slowly added to the solution at room temperature, and the mixture is thereafter subjected to the same treatment as in Example 27, giving 2.3 g of 2-oxo-3-cyclopentylpropyl-p-ethoxybenzene sulfonate (Compound 172), m.p. 36° to 36.5° C.

Yield 70.5%.

MS (M+): 326

H-NMR (CDCl$_3$) δ(ppm): 7.85 d (2H), 6.98 d (2H), 4.44 s (2H), 4.08 q (2H), 2.47 d (2H), 2.30–0.85 m (12H).

Elementary analysis:

|  | C | H |
| --- | --- | --- |
| Calcd. for C$_{16}$H$_{22}$SO$_5$ (%) | 58.88 | 6.79 |
| Found (%) | 58.61 | 7.17 |

EXAMPLE 30

Compounds 173 to 179 are prepared in the same manner as in Example 29.

EXAMPLE 31

A 1.54 g quantity of 4-tetrahydropyranyldiazomethyl ketone is dissolved in 50 ml of tetrahydrofuran, 2.1 g of benzenesulfonic acid monohydrate is slowly added to the solution at room temperature, and the mixture is stirred until nitrogen is no longer evolved. The reaction mixture is distilled in a vacuum to remove the solvent, 100 ml of ether is added to the residue for extraction, and the ethereal layer is washed with water, dried over anhydrous sodium sulfate and distilled in a vacuum. The oily product obtained is recrystallized from petroleum ether, affording 1.7 g of 2-oxo-2-(4-tetrahydropyranyl)-ethylbenzene sulfonate (Compound 180), m.p. 54° to 55° C. Yield 59.9%.

MS (M+): 284,

H-NMR (CDCl$_3$) δ(ppm): 8.20–7.45 m (5H), 4.62 s (2H), 4.20–3.80 m (2H), 3.55–3.20 m (2H), 3.00–2.60 m (1H), 1.85–1.45 m (4H).

Elementary analysis:

|   | C | H |
|---|---|---|
| Calcd. for C₁₃H₁₆SO₅ (%) | 51.99 | 5.37 |
| Found (%) | 51.66 | 5.51 |

EXAMPLE 32

Compounds 181 to 192 are prepared in the same manner as in Example 31.

EXAMPLE 33

A 1.5 g quantity of 1-diazo-5-chloro-2-n-pentanone is dissolved in 50 ml of ether, 2.1 g of benzenesulfonic acid monohydrate is slowly added to the solution at room temperature, and the mixture is stirred until nitrogen is no longer evolved. After the reaction, the ethereal layer is washed with water, dried over anhydrous sodium sulfate and distilled in a vacuum. The oily product obtained is stirred in ice for crystallization. The crystals are filtered off and recrystallized from ethanol/water to obtain 2.3 g of 2-oxo-5-chloro-n-pentyl-benzene sulfonate (Compound 193), m.p. 39° to 40° C. Yield 81.0%.

MS (M): 276,

H-NMR (CDCl₃) δ(ppm): 8.00–7.40 m (5H), 4.49 s (2H), 3.47 t (2H), 2.62 t (2H), 2.15–1.80 m (2H).

Elementary analysis:

|   | C | H |
|---|---|---|
| Calcd. for C₁₁H₁₃ClSO₄ (%) | 47.74 | 4.74 |
| Found (%) | 47.68 | 5.03 |

EXAMPLE 34

Compounds 194 to 200 are prepared in the same manner as in Example 1.

EXAMPLE 35

A 1.7 g quantity of 1-diazo-5-methoxycarbonyl-2-n-pentanone is dissolved in 50 cc of tetrahydrofuran, 2.5 g of p-ethoxybenzenesulfonic acid is slowly added to the solution at room temperature, and the mixture is thereafter treated in the same manner as in Example 33 to obtain an oily product, which is then recrystallized from ethanol/water, affording 2.2 g of 2-oxo-5-methoxycarbonyl-n-pentyl-p-ethoxybenzene sulfonate (Compound 201), m.p. 67° to 68° C. Yield 64.0%.

MS (M+): 344,

H-NMR (CDCl₃) δ(ppm): 7.85 d (2H), 7.00 d (2H), 4.45 s (2H), 4.08 q (2H), 3.64 s (3H), 2.55 t (2H), 2.30 t (2H), 2.05–1.65 m (2H), 1.44 t (3H).

Elementary analysis:

|   | C | H |
|---|---|---|
| Calcd. for C₁₅H₂₀SO₇ (%) | 52.33 | 5.86 |
| Found (%) | 52.35 | 5.85 |

EXAMPLE 36

Compounds 202, 203 and 205 to 207 are prepared in the same manner as in Example 35.

EXAMPLE 37

A 3.4 g quantity of 2-oxo-5-acetoxy-2-n-pentyl-2,4,6-trimethylbenzene sulfonate (Compound 207) is dissolved in 20 ml of ethanol, 30 ml of 2 N HCl is added to the solution with ice-cooling, and the mixture is stirred for 3 hours at room temperature. The reaction mixture is distilled in a vacuum to remove the ethanol, 50 ml of ether is added to the residue for extraction, and the ethereal layer is dried over anhydrous sodium sulfate and distilled in a vacuum. The resulting oily product is purified by silica gel column chromatography (developed with chloroform) to afford 0.9 g of 2-oxo-5-hydroxy-2-n-pentyl-2,4,6-trimethylbenzene sulfonate (Compound 204) in the form of a colorless transparent oil. Yield 30.2%.

MS (M+): 300,

H-NMR (CDCl₃) δ(ppm): 6.98 s (2H), 4.05–3.70 m (2H), 3.90 s (2H), 2.76 s (1H), 2.56 s (6H), 2.53 t (2H), 2.05–1.70 m (2H).

Table 3 shows the properties of Compounds 163 to 207 and percent triglycerides inhibition (TG).

TABLE 2

R₂(CH₂)ₙCOCHN₂

| Comp. No. | R₂ | n | Property | H—NMR —COCHN₂ | MS (M+) |
|---|---|---|---|---|---|
| A | ▷— | 0 | Oil | 5.35 | 110 |
| B | (cyclopentyl) | 1 | " | 5.20 | 152 |
| C | (cyclohexyl) | 0 | " | 5.25 | 152 |
| D | " | 1 | " | 5.20 | 166 |
| E | " | 2 | " | 5.23 | 180 |
| F | (tetrahydrofuryl) | 0 | " | 5.76 | 140 |
| G | (tetrahydropyranyl) | 0 | " | 5.30 | 154 |
| H | (phenyl) | 2 | " | 5.25 | 174 |
| I | —Cl | 3 | " | 5.25 | 146 |
| J | —I | 3 | " | 5.26 | 238 |
| K | —OCOCH₃ | " | " | 5.22 | 170 |
| L | —COOCH₃ | " | " | 5.29 | 170 |
| M | —OCH₃ | " | " | 5.25 | 142 |
| N | —NHCOOCH₂—(phenyl) | 5 | " | 5.23 | 261 |

TABLE 3
$$R_1SO_3CH_2CO(CH_2)_nR_2$$
| Comp. No. | $R_1$ | n | $R_2$ | M.P. (°C.) | Yield (%) | NMR —SO$_3$CHCO— | MS (M$^+$) | TG (%) |
|---|---|---|---|---|---|---|---|---|
| 163 | 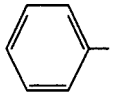 | 0 |  | Oil | 61.0 | 4.61 | 282 | |
| 164 | 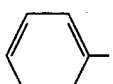 | 2 | 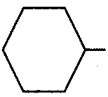 | 46–47 | 64.5 | 4.50 | 310 | 98 |
| 165 | 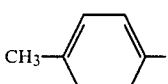 | 1 |  | 51–52 | 65.0 | 4.46 | 296 | |
| 166 | 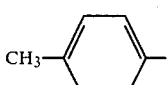 | 1 | 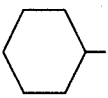 | Oil | 51.5 | 4.44 | 310 | |
| 167 | 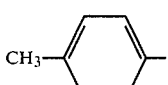 | 2 | 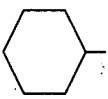 | 73.5 | 68.5 | 4.45 | 324 | 53 |
| 168 | 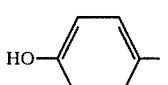 | 0 | 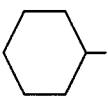 | 124 | 67.0 | 4.82 | 298 | |
| 169 | 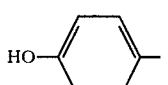 | 1 | 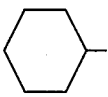 | 92–93 | 59.5 | 4.53 | 312 | |
| 170 | 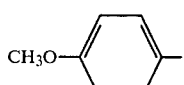 | 0 |  | Oil | 34.5 | 4.60 | 270 | |
| 171 | 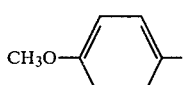 | 1 | 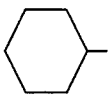 | Oil | 63.0 | 4.43 | 326 | |
| 172 | 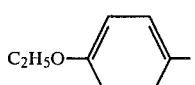 | 1 |  | 36–36.5 | 70.5 | 4.44 | 326 | |
| 173 | 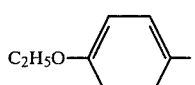 | 0 | 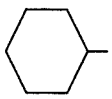 | 44–45 | 58.3 | 4.57 | 326 | |
| 174 | 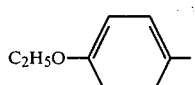 | 2 | 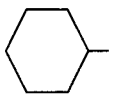 | 44 | 53.5 | 4.45 | 354 | 100 |

TABLE 3-continued $R_1SO_3CH_2CO(CH_2)_nR_2$

| A | B | n | C | D | E | F | G | H |
|---|---|---|---|---|---|---|---|---|
| Comp. No. | $R_1$ | n | $R_2$ | M.P. (°C.) | Yield (%) | NMR —SO$_3$CHCO— | MS (M+) | TG (%) |
| 175 | 2,4,6-trimethylphenyl | 0 | cyclopropyl | 82.3 | 41.2 | 4.55 | 282 | |
| 176 | 2,4,6-trimethylphenyl | 0 | cyclohexyl | 95–96 | 67.5 | 4.49 | 324 | |
| 177 | 2,4,6-trimethylphenyl | 1 | cyclohexyl | 36–37 | 68.3 | 4.40 | 338 | |
| 178 | 2,3,4,6-tetramethylphenyl | 1 | cyclopentyl | 92–93 | 57.4 | 4.38 | 338 | |
| 179 | 4-chlorophenyl | 0 | cyclohexyl | 69.5–70 | 55.3 | 4.62 | 316 | |
| 180 | phenyl | 0 | tetrahydropyran-4-yl | 54–55 | 59.9 | 4.62 | 284 | |
| 181 | 4-methylphenyl | 0 | tetrahydrofuran-2-yl | 103–106 | 25.0 | 4.03q (J = 9.0) | 284 | |
| 182 | 4-methoxyphenyl | 0 | tetrahydrofuran-2-yl | 81–83 | 20.0 | 4.02q (J = 8.5) | 300 | |
| 183 | 4-hydroxyphenyl | 0 | tetrahydropyran-4-yl | 154–155 | 50.5 | 4.54 | 300 | |
| 184 | 4-ethoxyphenyl | 0 | tetrahydropyran-4-yl | 57–58 | 55.3 | 4.53 | 328 | |

TABLE 3-continued $R_1SO_3CH_2CO(CH_2)_nR_2$

| A | B | n | C | D | E | F | G | H |
|---|---|---|---|---|---|---|---|---|
| Comp. No. | $R_1$ | n | $R_2$ | M.P. (°C.) | Yield (%) | NMR $-SO_3CHCO-$ | MS ($M^+$) | TG (%) |
| 185 | 2,4,6-tri-CH₃-phenyl | 0 | tetrahydropyran-2-yl | 106-106.5 | 23.0 | 4.01q (J = 9.0) | 312 | |
| 186 | 2,4,6-tri-CH₃-phenyl | 0 | tetrahydropyran-4-yl | 63.5-64.5 | 63.5 | 4.48 | 326 | |
| 187 | 4-CH₃-phenyl | 2 | phenyl | 72-73 | 71.0 | 4.42 | 318 | 94 |
| 188 | 4-Cl-phenyl | 2 | phenyl | 82-83 | 68.0 | 4.49 | 338 | 95 |
| 189 | 4-CH₃-phenyl | 0 | phenyl | 87 | 63.5 | 5.20 | 290 | |
| 190 | 4-CH₃-phenyl | 1 | 4-CH₃-phenyl | 55-56 | 51.0 | 4.50 | 318 | |
| 191 | 4-CH₃-phenyl | 0 | furan-2-yl | 57-58 | 40.0 | 5.00 | 280 | |
| 192 | 3-COOH-phenyl | 2 | phenyl | 120-121 | 60.0 | 4.53 | 348 | |
| 193 | phenyl | 3 | —Cl | 39-40 | 81.0 | 4.49 | 276 | |
| 194 | phenyl | 3 | —OCH₃ | Oil | 71.5 | 4.49 | 272 | |
| 195 | phenyl | 3 | —OCOCH₃ | Oil | 61.0 | 4.50 | 300 | 62 |

TABLE 3-continued
$R_1SO_3CH_2CO(CH_2)_nR_2$
| Comp. No. | $R_1$ | n | $R_2$ | M.P. (°C.) | Yield (%) | NMR —$SO_3CHCO$— | MS (M.+) | TG (%) |
|---|---|---|---|---|---|---|---|---|
| 196 | 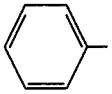 | 3 | —COOCH$_3$ | " | 70.0 | 4.50 | 300 | 77.9 |
| 197 | 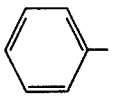 | 5 | —NHCOOCH$_2$— | " | 45.5 | 4.47 | 419 | |
| 198 | CH$_3$—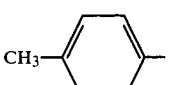— | 3 | —COOCH$_3$ | " | 66.0 | 4.48 | 314 | |
| 199 | CH$_3$—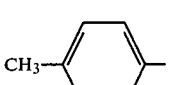— | 5 | —NHCOOCH$_2$— | 47–49 | 52.0 | 4.43 | | 4.33 |
| 200 | CH$_3$—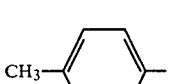— | 3 | —OCOCH$_3$ | Oil | 70.7 | 4.49 | | 3.14 |
| 201 | C$_2$H$_5$O—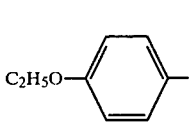— | 3 | —COOCH$_3$ | 67–68 | 64.0 | 4.45 | 344 | |
| 202 | 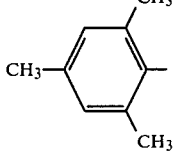 | 3 | —Cl | Oil | 81.5 | 4.42 | 318 | |
| 203 | 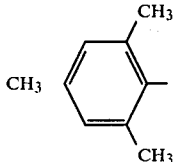 | 3 | —I | " | 53.5 | 4.41 | 410 | |
| 204 | 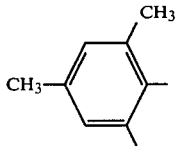 | 3 | —OH | " | 30.2 | 3.90 | 300 | |
| 205 | 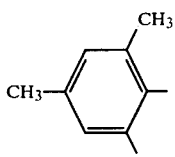 | 3 | —OCH$_3$ | " | 67.5 | 4.39 | 314 | |

TABLE 3-continued $R_1SO_3CH_2CO(CH_2)_nR_2$

| Comp. No. | $R_1$ | n | $R_2$ | M.P. (°C.) | Yield (%) | NMR $-SO_3CHCO-$ | MS ($M^+$) | TG (%) |
|---|---|---|---|---|---|---|---|---|
| 206 | 2,4,5-trimethylphenyl | 3 | $-COOCH_3$ | " | 63.0 | 4.43 | 342 | |
| 207 | 2,4,5-trimethylphenyl | 3 | $-OCOCH_3$ | 62.5–63.5 | 60.5 | 4.40 | 342 | |

Compounds of the formula (I) of this invention are tested for esterase inhibiting activity and chymotripsin inhibiting activity with the following results.

1. Esterase inhibiting activity

A 10 micromole quantity of methyl butyrate in a 50% ethanol solution is added as a substrate to a specified amount of buffer solution containing 0.1 mole of trishydrochloric acid (pH 8.0). To the mixture is further added a 50% ethanol solution of the compound of the invention, immediately followed by addition of an esterase solution prepared from a purified microsome fraction of the liver of a rat (adjusted to hydrolyze 9 micromoles of methyl butyrate at 37° C. in one hour) as an enzyme solution. The mixture is reacted at 37° C. for 60 minutes.

After the reaction, alkaline hydroxylamine is added to the mixture to form a hydroxyamic acid derivative of methyl butyrate, and a ferric salt is added to the derivative. The resulting red color is colorimetrically determined (at a wavelength of 540 nm) to determine the amount of remaining methyl butyrate. The esterase inhibiting ratios of the present compound at least at three concentrations are plotted as ordinate, and the logarithms of the concentrations as abscissa to obtain a line, which gives the 50% inhibition concentration ($IC_{50}$).

2. Chymotripsin inhibiting activity

Chymotripsin (0.1 unit) serving as an enzyme solution is added to a specified quantity of buffer solution containing 0.1 mole of trishydrochloric acid (pH 8.0). To the mixture is further added a 50% ethanol solution of the compound of the invention so that the resulting mixture contains the compound in a concentration of $1 \times 10^{-4}$ mole. The mixture is reacted at 37° C. for 20 minutes.

On completion of the reaction, 10 micromoles of N-acetyl-L-thyrosine ethyl ester (ATEE) serving as a substrate is added to the mixture, and the resulting mixture is reacted at 37° C. for 30 minutes.

After the completion of the reaction, the amount of remaining ATEE is determined by the same hydroxamic acid method as above. The percent chymotripsin inhibition is given by $$\text{Percent inhibition} = \frac{A - B}{A} \times 100$$

wherein A is the amount of hydrolyzed esters in the reaction system not containing the compound of the invention, and B is the amount of hydrolyzed esters in the reaction system containing the present compound.

Table 4 shows the $IC_{50}$ values of compounds of the invention for esterases and percent chymotripsin inhibition thereof.

Table 4 shows that the compounds of the invention act to inhibit esterases and chymotripsin and are useful as antilipemic agents, anti-inflammatory agents and immunity controlling agents.

TABLE 4

| Compd. No. | $IC_{50}$ for esterases ($\times 10^{-6}$ mole) | Percent chymotripsin inhibition |
|---|---|---|
| 1 | 12.0 | — |
| 5 | 3.6 | 17 |
| 8 | 0.072 | 100 |
| 9 | 0.068 | 96 |
| 10 | 0.0076 | 14 |
| 14 | 0.52 | 25 |
| 18 | 1.6 | 77 |
| 19 | 3.4 | 100 |
| 27 | 0.67 | 17 |
| 28 | 0.23 | 15 |
| 31 | 0.017 | 100 |
| 32 | 0.35 | 0.4 |
| 37 | 0.15 | 91 |
| 38 | 0.10 | 45 |
| 47 | 0.59 | 67 |
| 50 | 21 | 31 |
| 56 | 1.0 | 50 |
| 62 | 0.029 | 93 |
| 66 | 2.6 | 100 |
| 73 | 1.0 | 13 |
| 78 | 0.00063 | 72 |
| 80 | 0.000032 | 55 |
| 86 | 0.12 | 14 |
| 90 | 0.0026 | 13 |
| 96 | 0.00016 | 12 |
| 98 | 0.000027 | 26 |
| 101 | 0.03 | 23 |
| 111 | 0.28 | 4 |
| 116 | 1.3 | 0 |
| 120 | 0.3 | 35 |
| 129 | 7 | 30 |
| 130 | 4 | 52 |
| 134 | 560 | 2 |
| 135 | 56 | 10 |
| 137 | 10 | 14 |
| 138 | 4.2 | 67 |
| 143 | 2 | 79 |
| 145 | 3.3 | 87 |
| 149 | 1 | 7 |
| 151 | 32 | 8 |

TABLE 4-continued

| Compd. No. | IC$_{50}$ for esterases ($\times 10^{-6}$ mole) | Percent chymotripsin inhibition |
|---|---|---|
| 153 | 0.64 | 9 |
| 158 | 0.4 | 17 |
| 162 | 2 | 32 |
| 163 | 1.6 | 13 |
| 164 | 2.2 | 100 |
| 165 | 4.4 | 90 |
| 166 | 3.5 | 98 |
| 167 | 3.1 | 100 |
| 169 | 0.8 | — |
| 176 | 0.8 | — |
| 177 | 0.2 | 10 |
| 179 | 1.5 | 32 |
| 186 | 32 | — |
| 187 | 14 | 100 |
| 188 | 25 | 100 |
| 193 | 0.82 | 46.8 |
| 194 | 2.4 | 3.2 |
| 195 | 26 | 22.2 |
| 196 | 6.8 | 65.3 |
| 197 | 30 | 47 |
| 201 | 170 | 33 |
| 205 | 1.5 | 10 |

What is claimed is:

1. A method of treating a patient having hyperlipidemia, said method comprising administering to said patient a therapeutically effective amount of a compound of the formula $R_1SO_3CH_2CO(CH_2)_nR_2$ wherein $R_1$ is alkyl having 1 to 4 carbon atoms, alkoxyalkyl having 2 to 6 carbon atoms, phenylalkyl, cycloalkyl or aryl (which is phenyl or naphthyl) with or without a substituent (which is alkyl having 1 to 12 carbon atoms, lower alkoxy, halogen, hydroxyl, carboxyl, acetamido, nitro or ethylenedioxymethyl), $R_2$ is alkyl having 1 to 15 carbon atoms, alkenyl having 2 to 15 carbon atoms, halogen, hydroxyl, lower alkoxy, lower alkoxycarbonyl, $C_2$ to $C_6$ acyloxy, carbobenzoxyamino, cycloalkyl having 3 to 6 carbon atoms, cyclic alkylether having 2 to 5 carbon atoms or cyclic alkenylether having 2 to 5 carbon atoms, or phenyl or naphthyl with or without lower alkyl substituent(s), and n is 0 or an integer of 1 to 6.

2. A method of treating an inflammation in a patient having an inflammation, said method comprising administering to said patient an anti-inflammatory amount of a compound of the formula $R_1SO_3CH_2CO(CH_2)_nR_2$ wherein $R_1$ is alkyl having 1 to 4 carbon atoms, alkoxyalkyl having 2 to 6 carbon atoms, phenylalkyl, cycloalkyl or aryl (which is phenyl or naphthyl) with or without a substituent (which is alkyl having 1 to 12 carbon atoms, lower alkoxy, halogen, hydroxyl, carboxyl, acetamido, nitro or ethylenedioxymethyl), $R_2$ is alkyl having 1 to 15 carbon atoms, alkenyl having 2 to 15 carbon atoms, halogen, hydroxyl, lower alkoxy, lower alkoxycarbonyl, $C_2$ to $C_6$ acyloxy, carbobenzoxyamino, cycloalkyl having 3 to 6 carbon atoms, cyclic alkylether having 2 to 5 carbon atoms, cycllic alkenylether having 2 to 5 carbon atoms, or phenyl or naphthyl with or without lower alkyl substituent(s), and n is 0 or an integer of 1 to 6.

3. A method according to claim 1, wherein said cyclic ethers contain 4 or 5 carbon atoms.

4. A method according to claim 2, wherein said cyclic ethers have 4 or 5 carbon atoms.

* * * * *